United States Patent [19]

Badger

[11] Patent Number: 5,482,959
[45] Date of Patent: Jan. 9, 1996

[54] METHOD FOR DELAYING AIDS IN AN HIV INFECTED INDIVIDUAL BY ADMINISTRATION OF SUBSTITUTED AZASPIRANE COMPOUNDS

[75] Inventor: Alison M. Badger, Bryn Mawr, Pa.

[73] Assignee: SmithKline Beecham Corporation, Philadelphia, Pa.

[21] Appl. No.: 256,708

[22] PCT Filed: Jan. 27, 1993

[86] PCT No.: PCT/US93/00730

§ 371 Date: Jul. 21, 1994

§ 102(e) Date: Jul. 21, 1994

[87] PCT Pub. No.: WO93/14760

PCT Pub. Date: Aug. 5, 1995

[30] Foreign Application Priority Data

Jan. 28, 1992 [GB] United Kingdom .................... 9201803

[51] Int. Cl.⁶ ...................... A61K 31/405; A61K 31/445; C07D 213/00
[52] U.S. Cl. .......................... 514/409; 514/212; 514/278; 514/885
[58] Field of Search .................... 514/409, 212, 514/278, 885

[56] References Cited

U.S. PATENT DOCUMENTS

| 3,733,412 | 5/1973 | deBock | 514/409 |
| 4,411,904 | 10/1983 | Pattison | 424/267 |
| 4,963,557 | 10/1990 | Badger et al. | 514/278 |
| 5,395,848 | 3/1995 | Bugelski et al. | 514/419 |
| 5,399,553 | 3/1995 | Yokomoto et al. | 514/18 |

OTHER PUBLICATIONS

Badger et al, "Antiarthritic . . . Agents", Chem. Abstr., vol. 113, No. 21, Nov. 1990, No. 191085r, p. 696.

Badger et al, "Preparation . . . Immunosuppressants", Chem. Abstr., vol. 111, No. 17, pp. 702–703, No. 153616r, Oct. 1989.

El–Telbany, "Synthesis . . . Study. Part II", Chem. Abstr., vol. 86, No. 9, p. 419, Feb. 1977.

*Primary Examiner*—Arthur C. Prescott
*Attorney, Agent, or Firm*—Wayne J. Dustman; Stephen Venetianer; Edward T. Lentz

[57] ABSTRACT

Invented is a method of preventing or delaying the occurrence of acquired immunodeficiency syndrome (AIDS) in human immunodeficiency virus (HIV) seropositive humans which comprises administering to such human an effective therefor amount of a substituted azaspirane.

7 Claims, No Drawings

METHOD FOR DELAYING AIDS IN AN HIV INFECTED INDIVIDUAL BY ADMINISTRATION OF SUBSTITUTED AZASPIRANE COMPOUNDS

This application is a 371 of PCT/UP93/00730 Jan. 27, 1993.

This invention relates to a method of preventing or delaying the occurrence of acquired immunodeficiency syndrome (AIDS) in human immunodeficiency virus (HIV) seropositive humans which comprises administering to such human an effective therefore amount of a substituted azaspirane.

BACKGROUND OF THE INVENTION

The use of immunosuppressive/immunomodulatory agents has been shown to suppress viral replication. Specifically, immunomodulating CD8 lymphocytes have been shown to suppress replication of HIV in peripheral blood mononuclear cells (Waler et al. *Science*, 23:1563-6 (1986)) and activated CD8+ T cells have been shown to inhibit the replication of HIV in cultures of CD4+ cells from asymptomatic HIV seropositive individuals (Brinchmann et al. CD8+ T cells *J. Immunol.* 144 2961–2966 (1990)). Further, the immunosuppressive compound cyclosporin A (CsA) has demonstrated a protective effect in several animal models of viral infection. Particularly, chronic treatment with CsA before and after infection with LP-BM5 murine leukemia virus has proven effective against the development of immunodeficiency disease (Cerny, A. et al. *Eur. J. Immunol.* 21:1747-50 (1991)). Evidence that treatment of AIDS and HIV-seropositive non-AIDS patients with CsA increases T4 cells and inhibits lymphadenopathy has also been reported. (Andrieu et al. *Clin. Immunol. and Immumopathol.* 46:181–198 (1988)).

Badger, et al., U.S. Pat. No. 4,963,557 (Badger I) discloses compounds of the formula

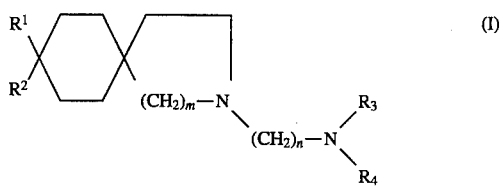

wherein: n is 3–7; m is 1 or 2; $R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms; $R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms; or a pharmaceutically acceptable salt or hydrate or solvate thereof.

Badger I discloses compounds of Formula I as a novel class of compounds which induce an immunomodulatory effect which is characterized by the stimulation of suppressor cell activity.

Badger I does not disclose the compounds of Formula I as agents for preventing or delaying the occurrence of AIDS in HIV seropositive humans.

SUMMARY OF THE INVENTION

This invention relates to a method of preventing or delaying the occurrence of AIDS in HIV seropositive humans which comprises administering to such mammal an effective therefor amount of a compound of the formula

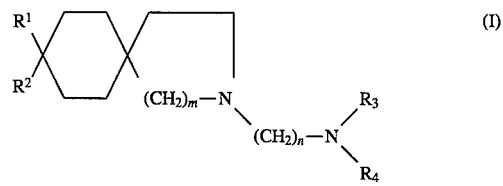

wherein:

n is 3–7;

m is 1 or 2;

$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;

$R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms;

or a pharmaceutically acceptable salt or hydrate or solvate thereof.

DETAILED DESCRIPTION OF THE INVENTION

The preparation of all compounds of Formula (I) and pharmaceutically acceptable salts, hydrates and solvates and formulations thereof is disclosed in U.S. Pat. No. 4,963,557, the entire disclosure of which is hereby incorporated by reference.

A preferred compound used in the novel method is the dihydrochloride salt of a compound of Formula (I) where $R^1$ and $R^2$ are propyl, $R^3$ and $R^4$ are methyl, m is 1 and n is 3 which is N,N-dimethyl-8,8-dipropyl-2-azaspiro[4,5]decane-2-propanamine dihydrochloride.

A preferred compound used in the novel method is a compound of Formula (I) where $R^1$ and $R^2$ are propyl, $R^3$ and $R^4$ are ethyl, m is 1 and n is 3 which is N,N-diethyl-8,8-dipropyl-2-azaspiro[4,5]decane-2-propanamine and salts thereof.

This invention discloses compounds of Formula (I) and pharmaceutically acceptable salts or hydrates or solvates thereof as being useful for preventing or delaying the occurrence of AIDS in HIV seropositive humans.

This invention relates to a method of delaying or preventing the occurrence of AIDS which comprises administering to an HIV seropositive human an effective therefor amount of a compound of Formula (I) or a pharmaceutically acceptable salt or hydrate or solvate thereof. A compound of Formula (I) or a pharmaceutically acceptable salt or hydrate or solvate thereof can be administered to such human in a conventional dosage form prepared by combining a compound of Formula (I) or a pharmaceutically acceptable salt or hydrate or solvate thereof, with a conventional pharmaceutically acceptable carrier or diluent according to known techniques, such as those described in Badger (I), U.S. Pat. No. 4,963,557.

It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt or hydrate or solvate thereof is administered to an HIV seropositive human in an amount sufficient to prevent or delay the occurrence of AIDS.

The route of administration of the Formula (I) compound is not critical but is usually oral or parenteral, preferably oral.

The term parenteral as used herein includes intravenous, intramuscular, subcutaneous, intranasal, intrarectal, transdermal, intravaginal or intraperitoneal administration. The subcutaneous and intramuscular forms of parenteral administration are generally preferred. The daily parenteral dosage regimen will preferably be from about 0.01 mg/kg to about 10 mg/kg of total body weight, most preferably from about 0.1 mg/kg to about 1 mg/kg. Preferably, each parenteral dosage unit will contain the active ingredient in an amount of from about 0.1 mg to about 100 mg.

The compounds of Formula (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

The daily oral dosage regimen will preferably be from about 0.01 mg/kg to about 10 mg/kg of total body weight. Preferably each oral dosage unit will contain the active ingredient in an amount of from about 0.1 mg to about 100 mg.

While it is possible for an active ingredient to be administered alone, it is preferable to present it as a pharmaceutical formulation.

It will be recognized by one of skill in the art that the optimal quantity and spacing of individual dosages of a compound of formula (I) or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt or hydrate or solvate thereof given per day and duration of therapy, can be ascertained by those skilled in the art using conventional course of treatment determination tests.

In addition, the compounds of the present invention can be co-administered with further active ingredients, such as other compounds known to prevent or delay the occurrence of AIDS in HIV seropositive humans such as retrovir (the brand name for zidovudine, formerly called azidothymidine (AZT)).

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1

CAPSULE COMPOSITION

An oral dosage form for administering Formula (I) compounds is produced by filing a standard two piece hard gelatin capsule with the ingredients in the proportions shown in Table I, below.

TABLE I

| INGREDIENTS | AMOUNTS |
| --- | --- |
| N,N-dimethyl-8,8-dipropyl-2-azaspiro[4,5]decane-2-propanamine dihydrochloride | 25 mg |
| Lactose | 55 mg |
| Talc | 16 mg |
| Magnesium Stearate | 4 mg |

EXAMPLE 2

INJECTABLE PARENTERAL COMPOSITION

An injectable form for administering Formula (I) compounds is produced by stirring 1.5% by weight of N,N-dimethyl-8,8-dipropyl-2-azaspiro[4,5]decane-2-propanamine dihydrochloride in 10% by volume propylene glycol in water.

EXAMPLE 3

Tablet Composition

The sucrose, calcium sulfate dihydrate and Formula (I) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| N,N-diethyl-8,8-dipropyl-2-azaspiro[4,5]decane-2-propanamine dihydrochloride | 20 mg |
| calcium sulfate dihydrate | 30 mg |
| sucrose | 4 mg |
| starch | 2 mg |
| talc | 1 mg |
| stearic acid | 0.5 mg |

What is claimed is:

1. A method for preventing or delaying the occurrence of acquired immunodeficiency syndrome (AIDS) in human immunodeficiency virus (HIV) seropositive humans which comprises administering to such human an effective therefor amount of a compound of the formula

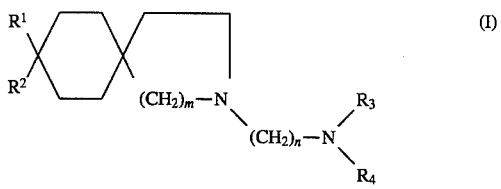

wherein:
n is 3–7;
m is 1 or 2;
$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;

$R^3$ and $R^4$ are the same or different and are selected from hydrogen or straight chain alkyl having 1–3 carbon atoms; or $R^3$ and $R^4$ are joined together with the nitrogen to form a heterocyclic group having 5–8 atoms;

or a pharmaceutically acceptable salt or hydrate or solvate thereof.

2. The method of claim 1 wherein the compound is N,N-diethyl-8,8-dipropyl-2-azaspiro[4,5]decane-2-propanamine;

or a pharmaceutically acceptable salt, hydrate or solvate thereof.

3. The method of claim 1 wherein the compound is administered orally.

4. The method of claim 3 wherein from about 0.01 mg/kg to about 10 mg/kg of compound is administered per day.

5. The method of claim 1 wherein the compound is administered parenterally.

6. The method of claim 5 wherein from about 0.01 mg/kg to about 10 mg/kg of compound is administered per day.

7. The method of claim 1 wherein the compound is N,N-dimethyl-8,8-dipropyl-2-azaspiro[4,5]decane-2-propanamine;

or a pharmaceutically acceptable salt hydrate of solvate thereof.

* * * * *